US005466220A

United States Patent [19]

Brenneman

[11] Patent Number: 5,466,220

[45] Date of Patent: Nov. 14, 1995

[54] DRUG VIAL MIXING AND TRANSFER DEVICE

[75] Inventor: Rodney Brenneman, Lake Oswego, Oreg.

[73] Assignee: Bioject, Inc., Portland, Oreg.

[21] Appl. No.: 208,620

[22] Filed: Mar. 8, 1994

[51] Int. Cl.$^6$ .................. A61M 37/00

[52] U.S. Cl. .................. 604/87; 604/411

[58] Field of Search .................. 604/56, 82–90, 604/92, 208, 248, 403, 407, 410, 413, 416, 411; 141/27, 26, 25, 94, 98, 391, 104

[56] References Cited

U.S. PATENT DOCUMENTS

| | | | |
|---|---|---|---|
| 2,584,397 | 2/1952 | Pitman | 604/413 |
| 3,343,538 | 9/1967 | Morley | 604/122 |
| 4,252,159 | 2/1981 | Maki | 141/27 |
| 4,433,974 | 2/1984 | Bischof | 604/410 |
| 4,434,820 | 3/1984 | Glass | 604/208 |
| 4,516,967 | 5/1985 | Kopfer | 604/87 |
| 4,564,054 | 1/1986 | Gustavsson | 604/411 |
| 4,568,346 | 2/1986 | van Dijk | 604/88 |
| 4,856,567 | 8/1989 | Cosmai | 604/405 |
| 4,900,322 | 2/1990 | Adams | 604/248 |
| 5,304,165 | 4/1994 | Haber et al. | 604/411 |

OTHER PUBLICATIONS

Lyophilization of Pharmaceuticals in Prefilled Syringes, Vetter, H.; *Drugs Made in Germany*, vol. XXVIII, 38–42 (1985).

"Hotline" article entitled Prefilled Suringe System Promotes Standardization *Medical Product Mfg. News*, vol. 8 No. 8, 6, Oct. 1992.

Brochure entitled, "For Medical Device Applications" regarding 'Intravenous devices' Mobay Corporation, p. 8, 1987.

Vetter Lyo–Ject™ product brochure entitled, "The complete delivery system" Pharma–Turm Inc.

*Primary Examiner*—C. Fred Rosenbaum
*Assistant Examiner*—N. Kent Gring
*Attorney, Agent, or Firm*—Lyon & Lyon

[57] ABSTRACT

A drug vial mixing and transfer device having a piercing connector or a syringe attached to the end of one or more ports with interconnecting fluid passageways. Further, the piercing connector is used to support and penetrate standard glass drug vials filled with powder or lyophilized drugs or liquid diluent, while the syringe is used to transfer liquid diluent and drug solutions between the vials and the syringe advantageously within a sealed system.

13 Claims, 3 Drawing Sheets

DRUG VIAL MIXING AND TRANSFER DEVICE

FIELD OF THE INVENTION

This invention relates to medication drugs for injection, specifically to a drug vial mixing and transfer device.

BACKGROUND OF THE INVENTION

Certain medication drugs are known to have relatively short shelf life in solution. These drugs are often maintained in a powder or lyophilized form prior to administration. Many of the powdered and lyophilized drugs are currently packaged in standard glass vials which are sealed with a rubber stopper and a crimped metal cap. A liquid diluent, usually sterile water, must be added to reconstitute the drug before use. Typically, a measured amount of liquid diluent is drawn into a syringe from a diluent vial. The sealed vial of powdered or lyophilized drug is then accessed with a needle and syringe to add the liquid diluent. The vial is shaken to mix the drug into the liquid diluent. Then air, equivalent to the amount of liquid drug to be withdrawn, is injected into a vial. Finally, the reconstituted drug is withdrawn into the syringe for injection.

It is desirable to reconstitute powdered or lyophilized drugs, due to their relatively short shelf life in solution, just prior to injection. If these drugs are self injected by a patient, they must also be reconstituted by the patient. The reconstituting of these drugs, along with the corresponding syringe filling for injection purposes, would normally require the patient to use an exposed sharp needle and perform the manipulations involved in this process. These manipulations may, however, be difficult for older or impaired patients to perform. It also presents the possibility of error, or contamination, should a recommended sterile procedure not be followed exactly.

Various related medication mixing devices have been known in the past. One type of these devices utilizes a "bottomless vial" concept for delivering lyophilized or powder-filled drugs with a needle and syringe. The basic concept is for the drug manufacturer to powder-fill or lyophilize the drug directly inside a bottomless vial. A second bottomless vial filled with a liquid diluent is then connected in front of the bottomless vial, using the plunger handle as the docking link. By pushing the liquid diluent vial with the plunger the fluid is transferred into the drug vial. The plunger handle and liquid diluent vial are then disconnected. The plunger handle is then reattached to the plunger end of the bottomless vial, and after attaching a needle, an injection is administered.

Another type of device utilizes a dual-compartment glass syringe. The rear compartment contains the liquid diluent, and the front compartment contains the powdered or lyophilized drug. The sidewall of the syringe contains a groove just forward of the stopper between chambers. As the plunger is pushed, the two stoppers and the fluid move forward until the groove in the side wall allows leakage of the fluid around the front stopper and into the drug chamber. The powder or lyophilized drug and liquid diluent are mixed and then the injection is administered.

Although these devices, along with others, may be useful, they are not without some shortcomings. For example, one of the disadvantages of the first type of device, the "bottomless vial" concept, is that it requires the use of non-standard medication vials and may be inconvenient for older and impaired patients to perform the necessary manipulations. A similar disadvantage of the second type of device, the dual-compartment syringe, is that it requires the use of a non-standard syringe. Moreover, the capabilities of both of these devices appear to be limited to the mixing of only two medications. Therefore, it would be desirable to have a medication mixing device which would enable an operator to easily mix a medication and liquid diluent, and then transfer the solution to a syringe without the need for a special syringe or vial, and that requires no exposed needle manipulation and reduces the possibility of contamination during the reconstituting and transfer processes.

SUMMARY OF THE INVENTION

The present drug vial mixing and transfer device preferably has one or more ports with interconnecting fluid passageways. The end of the ports are advantageously attached to either a piercing connector or a syringe. The piercing connector is used to support and penetrate standard glass drug vials filled with powdered or lyophilized drugs or liquid diluent, while the syringe is used to transfer liquid diluent and drug solutions between the vials and the syringe.

Preferably, the ports and connectors are mounted on a base wherein a stop cock type valve is used to coordinate communication between the fluid passageways of the different ports, and wherein the syringe and vials are held in place, prior to operation, by retainers mounted on the base. A preferred construction forms the retainers and base out of single piece molded plastic.

An object of this invention is to provide an improved drug vial mixing and transfer device.

Another object of this invention is to provide an improved drug vial mixing and transfer device that is a sealed mixing and transfer system and will eliminate the manipulations and sharp needle exposures normally associated with reconstituting powdered or lyophilized drugs.

Further objects and advantages of the present invention will become apparent from a consideration of the drawings and ensuing description.

DESCRIPTION OF THE PREFERRED EMBODIMENT

Figure 1:
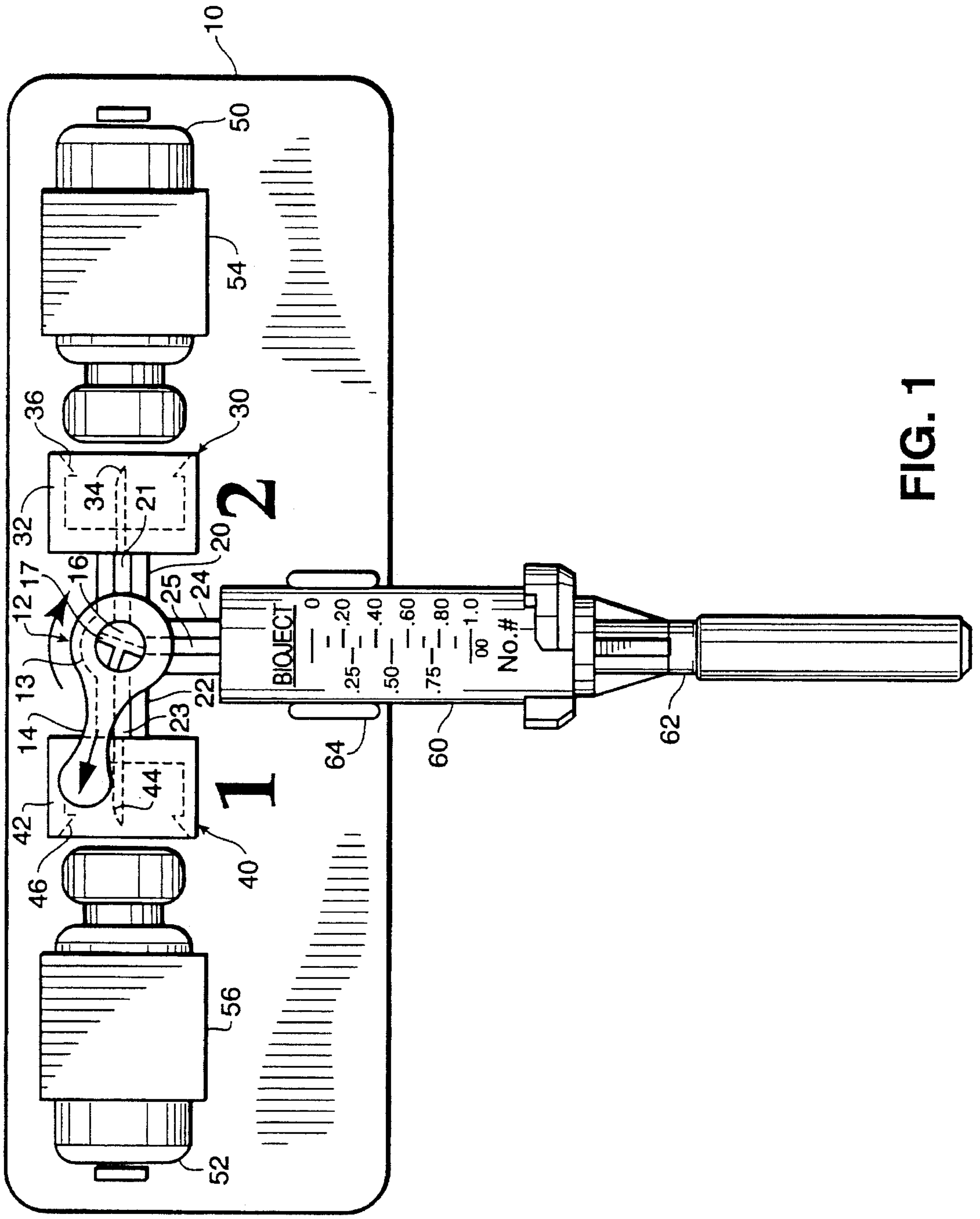
FIG. 1 is a top view of a preferred embodiment of a drug vial mixing and transfer device. The drug vial mixing and transfer device is depicted in its fully assembled pre-use unengaged configuration.

Referring now in detail to the drawings, therein illustrated in FIG. 1 is a top view of the preferred embodiment of a novel drug vial mixing and transfer device. This figure shows the drug vial mixing and transfer device comprising a base 10, which is substantially flat and rectangular, with a stop cock type valve 12 mounted on the face of the base 10.

The valve 12 comprises a valve body 13, a lever 14, a rotatable cylindrical stem 16, and three ports 20, 22, 24. The stem 16 is attached to the lever 14 and is axially located within the valve body 13. The three ports 20, 22, 24, with their corresponding fluid passageways 21, 23, 25, extend outwardly from the valve body 13. A "T" shaped fluid pathway 17 is formed within the stem 16. The fluid pathway 17 communicates with the fluid passageways 21, 23, 25, of the ports 20, 22, 24, controlling and directing the flow of fluid within the device. The ports 20, 22, 24 are configured in a "T" shape arrangement, such that, for exemplary purposes only, the two opposing ports 20, 22 generally form the horizontal member of the "T" and the third port 24 generally forms the vertical member of the "T." Although, for exemplary purposes the preferred embodiment comprises three ports configured in a "T" shape arrangement, other embodiments may vary the number of ports and their configuration to achieve substantially the same results.

Connected to the end of the horizontal port 20, extending to the right of the valve 12 at position "2", is a piercing connector 30. The piercing connector 30 comprises a cylindrically cup shaped housing 32, a piercing cannula 34, and an internal annular claw 36. The cannula 34 is axially fixed within the housing 32, thus forming a fluid pathway, through the housing 32, that communicates with the fluid passageway 21 of the port 20. The claw 36 is located annularly around the inner edge of the connector's 30 opening to act as a vial retainer. An identical configuration exists on the end of the opposing horizontal port 22 at position "1", wherein a piercing connector 40 is connected to the port 22. As above, the piercing connector 40 comprises a cylindrically cup shaped housing 42, a piercing cannula 44, and an annular claw 46. Also, the cannula 44 is axially fixed within the housing 42, thus forming a fluid pathway, through the housing 42, that communicates with the fluid passageway 23 of the port 22.

Axially aligned with the piercing connector 30, at position "2", is a vial retainer 54. The retainer 54 slidably retains a powdered or lyophilized drug vial 50 in place, prior to operation, at a predetermined spacing from the connector 30. An identical vial retainer 56 is axially aligned with the opposing piercing connector 40, at position "1". The retainer 56 also slidably retains a liquid diluent or sterile water vial 52 in place, prior to operation, at a predetermined spacing from the connector 40. The drug and liquid diluent vials 50, 52 can be of standard or non-standard construction.

A syringe 60 is connected to the end of the remaining vertical port 24 and communicates with the corresponding fluid passageway 25. The syringe 60 can be either a standard or non-standard syringe. A retainer 64 retains the syringe 60 in place on the face of the base 10. Preferably, the base 10 and the retainers 54, 56, 64 are formed of single piece molded plastic.

After slidably placing the drug and liquid diluent vials 50, 52 in their respective retainers 54, 56, and connecting the syringe 60 to the vertical port 24, the drug mixing and transfer device is packaged in a flexible protective packaging. This configuration creates a sealed sterile system.

In operation, the drug vial mixing and transfer device remains within its protective sterile packaging until the vials 50, 52 are pushed into their respective piercing connectors 30, 40. The patient, or operator, needing substantially only one hand, pushes the drug and liquid diluent vials 50, 52 into the piercing connectors 30, 40. The pushing action forces the drug and liquid diluent vials 50, 52 to overcome the annular claws 36, 46, such that the piercing cannulas 34, 44 penetrate the vials 50, 52. During the mixing and transfer process the annular claws 36, 46 retain the vials 50, 52 in place within the connectors 30, 40. Once the vials 50, 52 are in place the system is sealed and the flexible package can be removed. Furthermore, the system remains sealed during the entire reconstituting process, hence diminishing the potential of contamination by eliminating the need for swabbing vials before piercing, by eliminating manipulations with a sterile (but exposed) needle in open air, and by eliminating the need to individually access multiple vials for transfer of diluent and drugs.

To operate the drug vial mixing and transfer device, the lever 14 of the valve 12 is turned to position "1." This orients the "T" shaped fluid pathway 17, within the stem 16, such that the pathway 17 communicates with the fluid passageway 23 in the horizontal port 22 that is connected to the piercing connector 40 holding the sterile water vial 52, and the fluid passageway 25 in the vertical port 24 that is attached to the syringe 60. The drug vial mixing and transfer device is then held vertically, such that position "2" is oriented below position "1." The sterile water or liquid diluent in the vial 52 is then drawn into the syringe 60 by withdrawing a plunger 62 within the syringe 60.

The lever 14 is then turned to position "2" rotating the stem 16 within the valve 12. Air is vented between the vials 50, 52 as the lever 14 passes through a vertical position, relative to the "T" shape orientation of the ports 20, 22, 24, and the fluid pathway 17 within the stem 16 communicates with the fluid passageways 21, 23 in the horizontally opposed ports 20, 22. With the lever 14 in position "2", the fluid pathway 17 is oriented to communicate with the fluid passageway 21, in the horizontal port 20 connected to the piercing connector 30 holding the powdered or lyophilized drug vial 50, and the fluid passageway 25, in the vertical port 24 that attaches to the syringe 60. The drug vial mixing and transfer device is then inverted and held vertically, such that position "1" is oriented below position "2." The plunger 62 is then depressed to inject the sterile water or liquid diluent from the syringe 60 into the powdered or lyophilized drug vial 50. After mixing the solution, the reconstituted drug is withdrawn from the vial 50 into the syringe 60 by withdrawing the plunger 62. The syringe 60 is then removed from the drug vial mixing and transfer device ready to administer an injection. Thus, the reconstitution of the powdered or lyophilized drug, and the transfer of such solution to a syringe for injection, is accomplished within a sealed system without the manipulations, the sharp needle exposures, and the potential for contamination normally associated with reconstituting powdered or lyophilized drugs.

Figure 2:
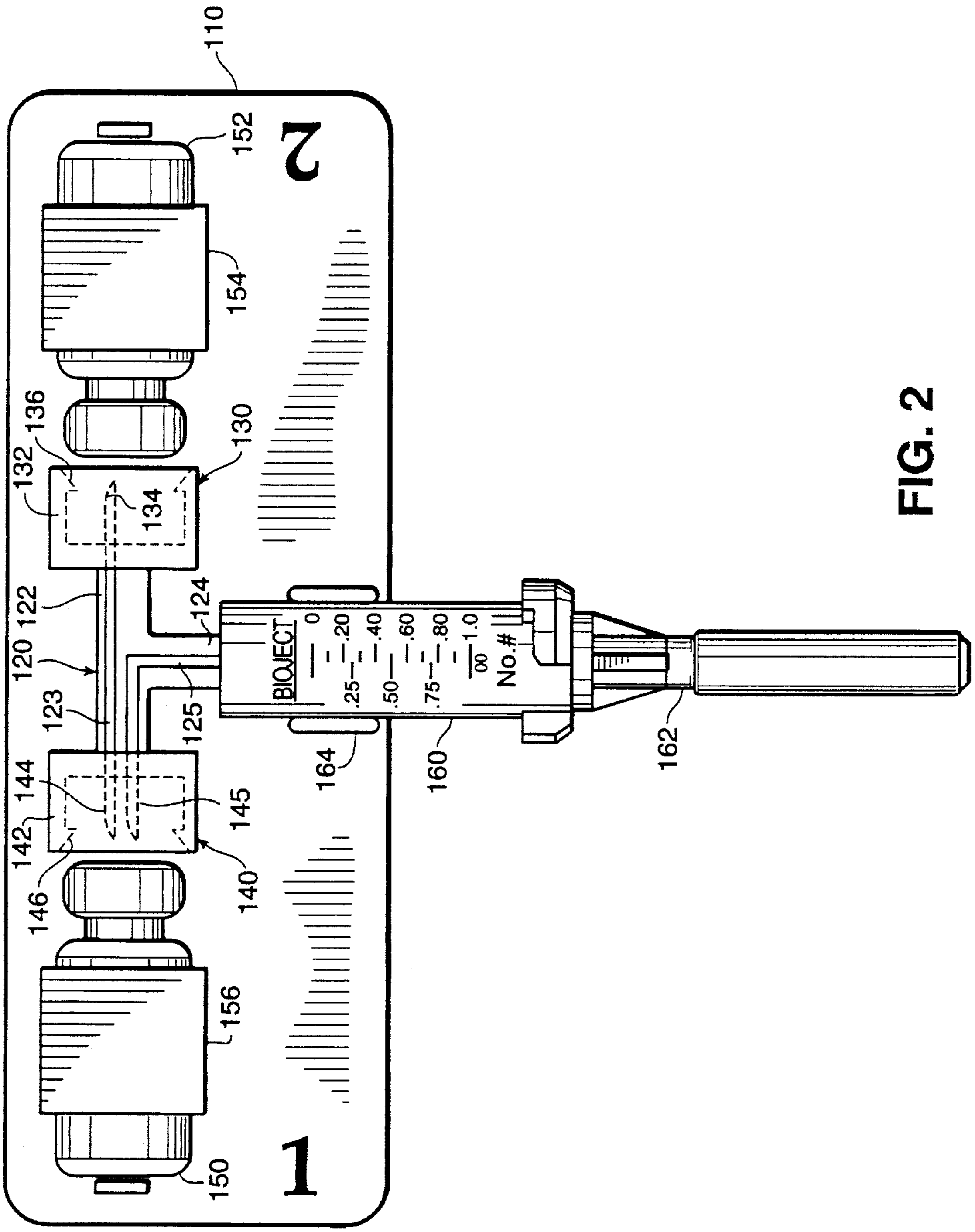
FIG. 2 is a top view of a second embodiment of a drug vial mixing and transfer device. The drug vial mixing and transfer device is depicted in its fully assembled pre-use unengaged configuration.

Referring now to FIG. 2, a top view of a second embodiment of the drug vial mixing and transfer device is shown. This figure shows the drug vial mixing and transfer device with a substantially similar layout to the preferred embodiment depicted in FIG. 1. The second embodiment, however, replaces the stop cock type valve concept of the preferred embodiment with a "T" shaped tri-port 120 configuration mounted on the face of a base 110. The tri-port 120 "T" contains two fluid passageways 123, 125; one of the passageways 123 traverses the horizontal member 122 of the tri-port 120 "T", while the other passageway 125 traverses the left half of the horizontal member 122 of the tri-port 120 "T" and then traverses down the vertical member 124 of the tri-port 120 "T."

Connected to the right end of the horizontal member 122 of the tri-port 120 is a connector 130, which, as in the preferred embodiment, is a piercing connector comprising a cylindrically cup shaped housing 132, a piercing cannula 134, and an annular claw 136. As above, the cannula 134 is axially fixed within the housing 132, thus forming a fluid pathway, through the housing 132, that communicates with the horizontally traversing fluid passageway 123. The claw 136 is also located annularly around the inner edge of the connector's 130 opening to act as a vial retainer.

As in the preferred embodiment, a substantially similar configuration exists on the opposing end of the horizontal member 122 of the tri-port 120, wherein a piercing connector 140 is connected to the tri-port 120. The connector 140 comprises a cylindrically cup shaped housing 142, a piercing cannula 144 that communicates with the horizontally traversing fluid passageway 123, and an annular claw 146. However, an additional piercing cannula 145 is fixed within the housing 142 of the connector 140. This cannula 145 forms a fluid pathway through the housing 142 that communicates with the fluid passageway 125 that traverses horizontally and vertically.

A syringe 160, standard or non-standard, is attached to the vertical member 124 of the tri-port 120 "T" and communicates with the corresponding vertically and horizontally traversing fluid passageway 125. The syringe 160 is held in place on the face of the base 110 by a retainer 164.

As in the preferred embodiment, two vial retainers 154, 156, attached to the base 110, are axially aligned with the piercing connectors 130, 140. A vial 152 containing liquid diluent or sterile water is slidably retained, at a predetermined spacing from the piercing connector 130 prior to operation, by the retainer 154 at position "2". Likewise, a vial 150 containing powdered or lyophilized drugs is slidably held in place, at a predetermined spacing from the piercing connector 140 prior to operation, by the retainer 156 at position "1."

After slidably placing the drug and liquid diluent vials 150, 152 into their respective retainers 154, 156 and connecting the syringe 160 to the vertical member 124 of the tri-port 120 "T", the drug mixing and transfer device is packaged in a flexible protective packaging. This configuration creates a sealed sterile system.

As in the preferred embodiment, the drug vial mixing and transfer device remains within its protective sterile packaging until the vials 150, 152 are pushed into the piercing connectors 130, 140. The patient, or operator, needing substantially only one hand, pushes the drug and liquid diluent vials 150, 152 into the piercing connectors 130, 140. The pushing action forces the drug and liquid diluent vials 150, 152 to overcome the annular claws 136, 146, such that the piercing cannulas 134, 144, 145 penetrate the drug and liquid diluent vials 150, 152. During the mixing and transfer operations the annular claws 136, 146 retain the vials 150, 152 in place within the connectors 130, 140. As above in the preferred embodiment, once in place, the system is sealed and the flexible package can then be removed. Remaining sealed during the entire reconstituting process, the system diminishes the potential of contamination during drug mixing and transferring of the solution between the vials 150, 152 and the syringe 160.

To operate, the drug vial mixing and transfer device is held vertically, such that position "1" is oriented below position "2." A plunger 162 within the syringe 160 is then withdrawn and depressed several times to pump the sterile water or liquid diluent from the vial 152 at position "2" into the powdered or lyophilized drug vial 150 at position "1." The sterile water or liquid diluent in the vial 152 enters the powder and lyophilized drug vial 150 as air from the drug vial 150 is forced back up into the diluent vial 152 with the forward plunger stroke, effectively equalizing the pressure between the two vials 150, 152.

After mixing the solution the drug vial mixing and transfer device is inverted and held vertically, such that position "2" is oriented below position "1". In this orientation, the reconstituted drug in the vial 150 at position "1" is withdrawn into the syringe 160 by withdrawing the plunger 162. The syringe 160 is then removed from the drug vial mixing and transfer device ready to administer an injection. As in the preferred embodiment, the reconstitution of the powdered or lyophilized drug, and the transfer of such solution to a syringe for injection, is accomplished within a sealed system without the manipulations, the sharp needle exposures, and the potential for contamination normally associated with reconstituting powdered or lyophilized drugs.

Figures 3, 4A, 4B:
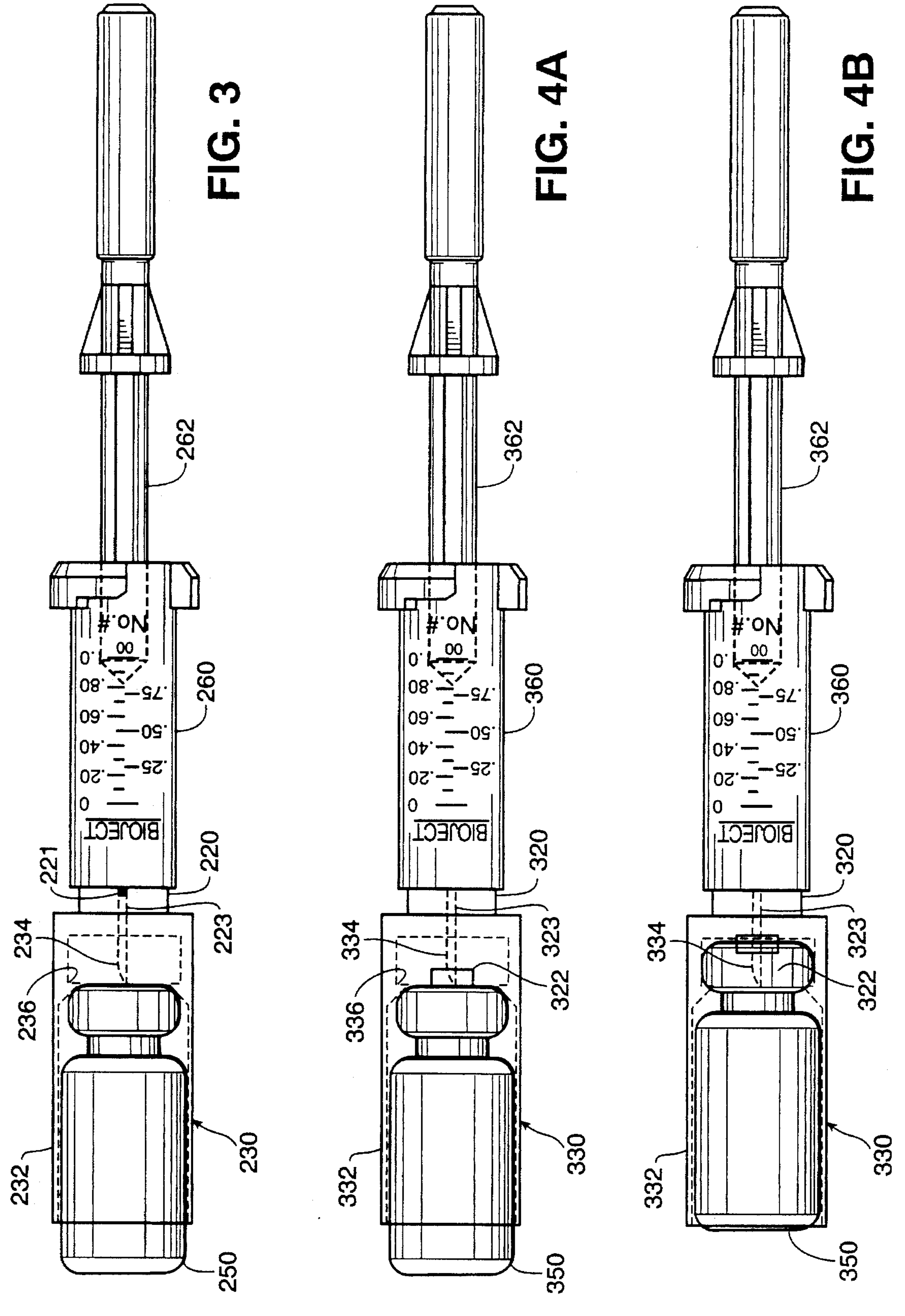
FIG. 3 is a top view of a third embodiment of a drug vial mixing and transfer device. The drug vial mixing and transfer device is depicted in its fully assembled pre-use unengaged configuration.
FIG. 4A is a top view of a modification of the third embodiment of a drug vial mixing and transfer device. The drug vial mixing and transfer device is depicted in its fully assembled pre-use unengaged configuration.
FIG. 4B is a top view of the drug vial mixing and transfer device shown in FIG. 4A. The drug vial mixing and transfer device is depicted in its fully assembled in-use engaged configuration.

Referring now to FIG. 3, a top view of a third embodiment of the drug vial mixing and transfer device is shown. This figure shows the drug vial mixing and transfer device comprising a piercing connector 230, a tubular port 220 connected to the piercing connector 230, and a syringe 260, standard or non-standard, attached to the tubular port 220. The piercing connector 230 is modified, from the preferred embodiment version, to comprise an elongated cylindrically cup shaped housing 232. The housing 232 acts to support a powdered or lyophilized drug vial 250 prior to operation. The connector 230 also includes a piercing cannula 234 and an annular claw 236. The cannula 234 is axially fixed within the housing 232, thus forming a fluid pathway, through the housing 232, that communicates with a fluid passageway 223 formed in the port 220. The claw 236 is also annularly located around the inner surface of the housing 232.

The drug vial mixing and transfer device is assembled by first filling the syringe 260 with a liquid diluent or sterile water and attaching the syringe 260 to the port 220. The fluid passageway 223, in the port 220, contains a pressure moveable plug 221 to prevent leakage of the liquid diluent prior to operation. Lastly, a vial 250, filled with powdered or lyophilized drug, is slidably placed within the housing 232 of the piercing connector 230. The annular claw 236, within the housing 232 of the connector 230, acts to prevent the vial 250 from communicating with the piercing cannula 234 prior to operation. This assembly is then packaged in a flexible protective packaging creating a sealed sterile system.

In operation the drug vial mixing and transfer device remains within its protective sterile packaging, as in the previous embodiments, until the drug vial 250 is pushed into the piercing connector 230. The patient, or operator, pushes the vial 250 into the piercing connector 220 such that the vial 250 overcomes the annular claw 236 and is penetrated by the piercing cannula 234. The claw 236 retains the vial 250 within the connector 230 during operation. As above, once the vial 250 is in place, the flexible package removed, the system is sealed during the entire reconstituting process, hence diminishing the potential of contamination.

To operate, a plunger 262 within the syringe 260 is depressed. This action generates sufficient pressure to dislodge the plug 221 in the fluid passageway 223 of the port 220 through the cannula 234 into the vial 250. With the fluid passageway 223 clear, the vial 250 is filled with the liquid diluent or sterile water from the syringe 260. After mixing the solution, the reconstituted drug is withdrawn from the vial 250 into the syringe 260 by withdrawing the plunger 262. The syringe 260 is then disconnected from the port 220 to administer an injection. As in the previously described embodiments, the reconstitution of the powdered or lyophilized drug, and the transfer of such solution to a syringe for injection, is accomplished within a sealed system without the manipulations, the sharp needle exposures, and the potential for contamination normally associated with reconstituting powdered or lyophilized drugs.

Referring now to FIG. 4A, a top view of a modification to the third embodiment (see FIG. 3) of the drug vial mixing and transfer device is shown. This figure shows substantially the identical components of the third embodiment of the drug vial mixing and transfer device comprising a piercing connector 330, a tubular port 320 connected to the piercing connector 330, and a syringe 360 attached to the tubular port 320. The housing 332 of the piercing connector 330 acts to support a powdered or lyophilized drug vial 350 prior to operation. The connector 330 also includes a piercing cannula 334 and an annular claw 336.

As in the third embodiment, the drug vial mixing and transfer device is assembled by first filling the syringe 360 with a liquid diluent or sterile water and attaching the syringe 360 to the port 320. However, the fluid passageway 323, in the port 320, remains unobstructed. Instead, a cap 322, fitted over the piercing end of the cannula 334, acts to plug the cannula 334 to prevent leakage of the liquid diluent prior to operation. Lastly, as above, a vial 350 filled with powdered or lyophilized drug, is slidably placed within the housing 332 of the piercing connector 330. The annular claw 336, within the housing 332 of the connector 330, acts to prevent the vial 350 from communicating with the piercing cannula 334 prior to operation. This assembly is then packaged in a flexible protective packaging creating a sealed sterile system.

In operation the drug vial mixing and transfer device remains within its protective sterile packaging, as in the previous embodiments, until the drug vial 350 is pushed into the piercing connector 330. The patient, or operator, pushes the vial 350 into the piercing connector 320 such that the vial 350 overcomes the annular claw 336 and contacts the cap 322 on the cannula 334. As seen in FIG. 4B, the pushing motion forces the cannula 334 to pierce the cap 322 and then the vial 350, and thus forces the cap 322 back along the cannula 334 as the cannula 334 penetrates the vial 350. The claw 336 retains the vial 350 within the connector 330 during operation. As above, once the vial 350 is in place, the flexible package removed, the system is sealed during the entire reconstituting process, hence diminishing the potential of contamination.

The operation is as noted above in regard to the third embodiment, and also as above, the reconstitution of the powdered or lyophilized drug, and the transfer of such solution to a syringe for injection, is accomplished within a sealed system without the manipulations, the sharp needle exposures, and the potential for contamination normally associated with reconstituting powdered or lyophilized drugs.

Thus, the drug vial mixing and transfer device of the present invention provides many benefits over the prior art. While the above description contains many specificities, these should not be construed as limitations on the scope of the invention, but rather as an exemplification of the preferred embodiments thereof. Many other variations are possible.

Accordingly, the scope of the present invention should be determined not by the embodiments illustrated above, but by the appended claims and their legal equivalents.

What is claimed is:

1. A drug mixing and transfer device comprising:

a base;

a valve attached to said base;

a plurality of ports with fluid passageways extending generally outwardly from said valve, said valve enabling fluid communication between the fluid passageways of said plurality of ports;

a piercing connector attached to each of said plurality of ports, said piercing connector being adapted to receive and penetrate a vial and to retain the vial in place during operation of the drug mixing and transfer device;

a retainer attached to said base and located in spaced relation to said piercing connector, said retainer being adapted to maintain the vial in spaced relation with said piercing connector prior to operation of the drug mixing and transfer device; and a syringe attaching port having a fluid passageway and extending generally outwardly from said valve, said valve enabling fluid communication between the fluid passageway of said syringe attaching port and the fluid passageways of said plurality of ports.

2. The drug mixing and transfer device of claim 1, wherein said retainer and said base are constructed of single piece molded plastic.

3. The drug mixing and transfer device of claim 1, wherein said valve comprises a stop cock type valve.

4. The drug mixing and transfer device of claim 3, wherein said stop cock type valve further comprises:

a valve body;

a lever;

a generally cylindrical stem attached to said lever and generally axially and rotatably located within said valve body; and a fluid passageway within said stem, said fluid passageway of said stem enabling fluid communication between the fluid passageways of said syringe attaching port and said plurality of ports.

5. The drug mixing and transfer device of claim 1, wherein said piercing connector further comprises:

a generally cylindrically cup shaped housing;

an annular claw attached generally annularly around the inner surface of said housing; and a piercing cannula generally fixed axially within said housing, said cannula forming a fluid pathway through said housing that communicates with the corresponding fluid passageway of said plurality of ports.

6. The drug mixing and transfer device of claim 1, further comparing a vial mounted in said retainer and filled with either a liquid diluent, a liquid drug, or a lyophilized drug.

7. A drug mixing and transfer device comprising:

a port having a fluid passageway therethrough;

a piercing connector attached to said port to receive and penetrate a vial;

a retainer extending from said piercing connector and adapted to maintain the vial in spaced relation with said piercing connector prior to operation of the drug mixing and transfer device;

a syringe attached to said port, said syringe being in fluid communication with the fluid passageway of said port; and a plug within said piercing connector to prevent leakage of liquid diluent from said syringe prior to operation.

8. The drug mixing and transfer device of claim 7, wherein said piercing connector further comprises:

a generally cylindrically cup shaped housing;

an annular claw attached generally annularly around inner surface of said housing; and a piercing cannula generally fixed axially within said housing, said cannula forming a fluid pathway through said housing that communicates with the fluid passageway of said port.

9. The drug mixing and transfer device of claim 7, further comprising a vial mounted in said retainer and filled with either a liquid diluent, a liquid drug, or a lyophilized drug.

10. A drug mixing and transfer device comprising:

a base;

a plurality of ports having interconnecting fluid passageways mounted on said base;

a plurality of piercing connectors respectively attached to said plurality of ports, each of said plurality of piercing connectors being adapted to receive and penetrate a vial;

a plurality of retainers mounted to said base and respectively located in spaced relation to said plurality of piercing connectors, each of said plurality of retainers being adapted to respectively maintain the vials in spaced relation with said plurality of piercing connectors prior to operation of the drug mixing and transfer device; and at least one syringe attaching port having a fluid passageway interconnected with said interconnecting fluid passageways of said plurality of ports.

11. The drug mixing and transfer device of claim 10, wherein said base and said plurality of retainers are constructed out of single piece molded plastic.

12. The drug mixing and transfer device of claim 10, wherein said piercing connector further comprises:

a generally cylindrically cup shaped housing;

an annular claw attached generally annularly around the inner surface of said housing; and a piercing cannula generally fixed axially within said housing, said cannula forming a fluid pathway through said housing that communicates with the corresponding fluid passageway of said plurality of ports.

13. The drug mixing and transfer device of claim 10, further comprising a vial mounted in each of said plurality of retainers and filled with either a liquid diluent, a liquid drug, or a lyophilized drug.

* * * * *

UNITED STATES PATENT AND TRADEMARK OFFICE

CERTIFICATE OF CORRECTION

PATENT NO. : 5,466,220

DATED : November 14, 1995

INVENTOR(S) : BRENNEMAN, Rodney

It is certified that error appears in the above-indentified patent and that said Letters Patent is hereby corrected as shown below:

Column 8, line 34, after "a" delete "lever" and insert --lever-- therefor.

Column 8, line 53, before "a" delete "comparing" and insert --comprising-- therefor.

Signed and Sealed this

Nineteenth Day of March, 1996

Attest:

Bruce Lehman

BRUCE LEHMAN

*Attesting Officer* *Commissioner of Patents and Trademarks*